(12) United States Patent
Homestad

(10) Patent No.: US 6,974,882 B2
(45) Date of Patent: Dec. 13, 2005

(54) PREPARATION OF IODIXANOL

(75) Inventor: Ole Magne Homestad, Lindesnes-Fabrikker (NO)

(73) Assignee: Amersham Health AS, Oslo (NO)

( * ) Notice: Subject to any disclaimer, the term of this patent is extended or adjusted under 35 U.S.C. 154(b) by 913 days.

(21) Appl. No.: 09/923,074

(22) Filed: Aug. 6, 2001

(65) Prior Publication Data

US 2002/0010368 A1 Jan. 24, 2002

Related U.S. Application Data

(63) Continuation of application No. PCT/GB00/00413, filed on Feb. 10, 2000.
(60) Provisional application No. 60/121,539, filed on Feb. 25, 1999.

(30) Foreign Application Priority Data

Feb. 11, 1999 (GB) .............................................. 9903109

(51) Int. Cl.⁷ ............................................ C07C 233/64
(52) U.S. Cl. .................... 564/153; 424/9.452
(58) Field of Search ....................... 564/153; 424/9.452

(56) References Cited

U.S. PATENT DOCUMENTS

| 3,816,521 A | | 6/1974 | Ueno et al. |
| 5,235,116 A | | 8/1993 | Fuller, Jr. |
| 5,349,085 A | * | 9/1994 | Hansen et al. .............. 564/153 |

FOREIGN PATENT DOCUMENTS

| EP | 0 108 638 A | | 5/1984 |
| EP | 0 108 638 B1 | | 7/1986 |
| WO | WO 98/08805 | | 3/1998 |
| WO | 98/23296 | * | 6/1998 |

* cited by examiner

*Primary Examiner*—Shailendra Kumar
(74) *Attorney, Agent, or Firm*—Li Cai

(57) ABSTRACT

A process for the preparation of iodixanol by dimerization of 5-acetamido-N,N'-bis(2,3-dihydroxypropyl)-2,4,6-triiodo-isophthalamide ("Compound A") in which, after the dimerization step, unreacted Compound A is precipitated from the reaction mixture and recovered for re-use. The process substantially increases the net yield of iodixanol and simplifies its purification.

9 Claims, No Drawings

PREPARATION OF IODIXANOL

This application is a continuation of PCT/GB00/00413, filed Feb. 10, 2000, and claims benefit of 60/121,539, filed Feb. 25, 1999.

This invention is concerned with the synthesis of iodixanol.

Iodixanol (1,3-bis(acetamido)-N,N'-bis[3,5-bis(2,3-dihydroxypropylaminocarbonyl)-2,4,6-triiodophenyl]-2-hydroxypropane) is a non-ionic X-ray contrast agent which is currently manufactured in large quantities. A number of methods are known for its preparation but these are all multistep processes and the cost of the final formulated product thus mainly depends on these processes. It is therefore important to optimise these processes for both economic and environmental reasons.

Three main processes are known for the preparation of iodixanol, all of which start with 5-nitroisophthalic acid. In the first process (NO 161358), the following route is used, via the final intermediate 5-acetamido-N,N'-bis(2,3-dihydroxypropyl)-2,4,6-triiodoisophthalamide ("Compound A"):

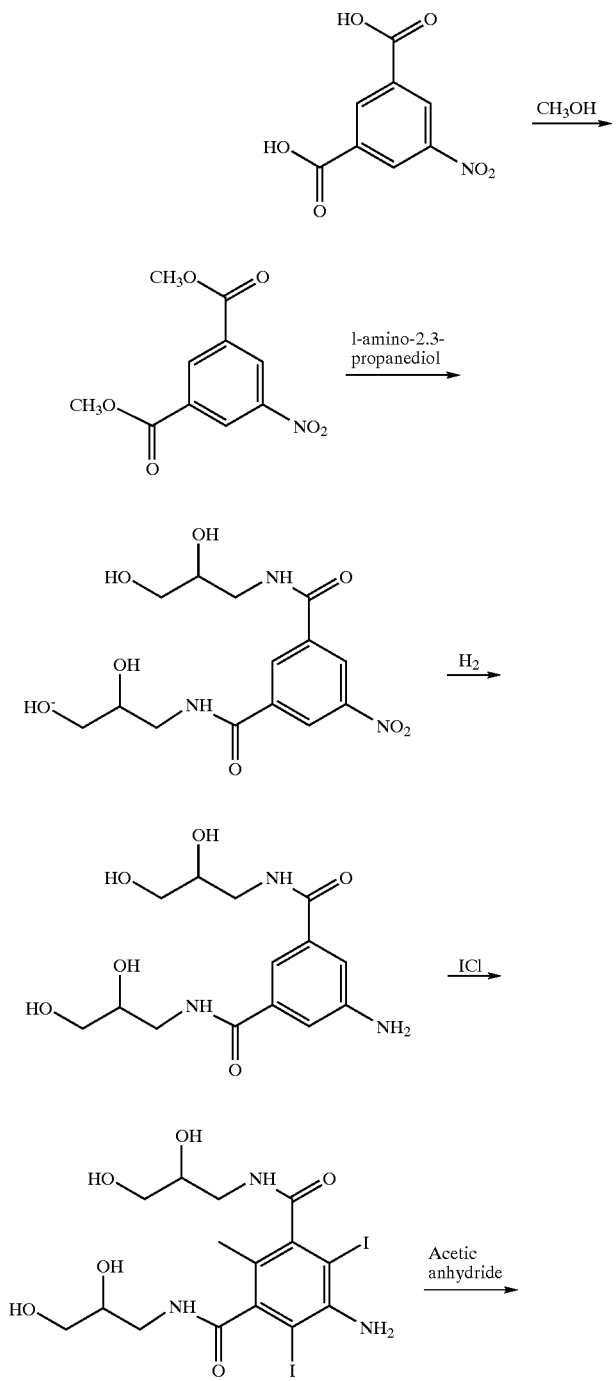

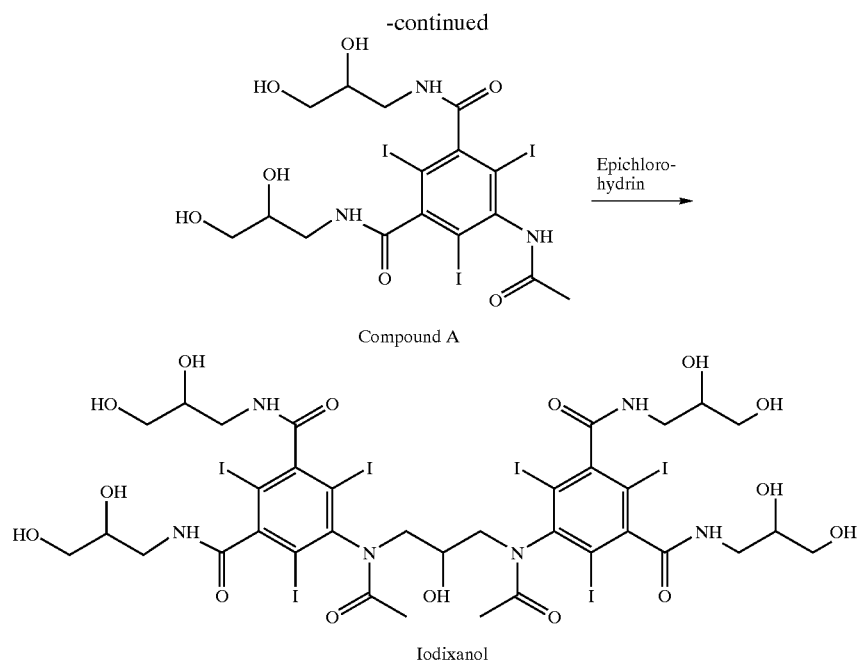

Compound A

Iodixanol

The problem with this process is that a yield of only 18% is reported in the given example, and the product is purified by preparative chromatography. When we have repeated the example, we have found that the low yield is due to incomplete conversion (dimerisation) of Compound A to iodixanol. After 40–60% of the starting material is consumed, over-alkylation of iodixanol starts to dominate over the desired reaction, causing the net content of iodixanol in the reaction mixture to decrease. In fact, 40–60% conversion to iodixanol seems to be the maximum obtainable. Due to this low conversion, common crystallisation techniques are not able to purify the product to the necessary level, and preparative liquid chromatography is the only way to obtain a pure product. The combination of low yields with an expensive purification method such as preparative chromatography is a serious disadvantage in an industrial process.

Priebe et. al. (*Acta Radiol.* 36 (1995), Suppl. 399, 21–31) describe another route which avoids the difficult last step of the above process. However, the route involves eight reaction steps from 5-nitroisophthalic acid, which is undesirable, and one of the steps includes chlorination with thionyl chloride, which is extremely corrosive. Also, the introduction of the iodine atoms takes place very early in the sequence, which is disadvantageous as iodine is the most expensive reagent in the process. The yield and final purification method for this route have not been reported.

The third route to iodixanol involves the synthesis of 5-amino-2,4,6-triiodoisophthalic acid (WO 96/37458) and then its dichloride (WO 96/37459), followed by conversion into Compound A (U.S. Pat. No. 5,705,692) and finally dimerisation as in the first process above. This method thus has the same disadvantages as the first, and also uses an undesirable acid chlorination step.

We have now surprisingly found that unreacted Compound A from one dimerisation batch, as produced for example in the first and third processes described above, can be recovered from the reaction mixture by a very simple process, and reused in a later batch. This increases the net yield from successive batches on an industrial scale dramatically. Additionally, the removal of most of the unreacted Compound A from the reaction mixture allows the expensive preparative liquid chromatography purification to be replaced by conventional crystallisation methods, still providing iodixanol suitable for pharmaceutical use.

The invention thus provides a process for the preparation of iodixanol by dimerisation of Compound A in which, after the dimerisation step, unreacted Compound A is precipitated from the reaction mixture and recovered for re-use.

The dimerisation step itself may be carried out as described in NO 161368 and WO 98/23296, for example using epichlorohydrin, 1,3-dichloro-2-hydroxypropane or 1,3-dibromo-2-hydroxypropane as the dimerisation agent. The reaction is usually carried out in a non-aqueous solvent such as a $C_{1-6}$ alcohol, preferably 2-methoxyethanol or methanol, and generally results in the conversion of 40–60% of Compound A to iodixanol. Dimerisation in pure water or mixtures of water and one or more alcohols (e.g. $C_{1-6}$-alkanols) is also possible.

Precipitation of Compound A from a non-aqueous reaction mixture can be effected after addition of water, for example in an amount of 1–2, preferably 1.3–1.8 L/kg Compound A used as starting material. If water is present in the reaction mixture, the amount of water added for precipitation can be reduced accordingly. An alcoholic co-solvent (e.g. a $C_{1-6}$ alkanol such as methanol) may additionally be used, for example in an amount of 0.5–2, preferably 0.8–1.5 L/kg Compound A used as starting material. In some instances, traces of undissolved material remain after the addition of water and alcohol and these can be dissolved by addition of alkali, e.g. sodium hydroxide. The pH of the solution is then adjusted to about 10–11 by addition of an acid, e.g. hydrochloric acid, to provoke precipitation of unreacted Compound A and if necessary the temperature can be adjusted to 15–40 C., preferably 18–30 C. The solution is optionally seeded with crystals of Compound A to initiate the precipitation of Compound A, while the iodixanol formed stays in solution.

Further addition of acid to a pH of 2–5, preferably 3–4, can increase the yield of the recovery process by increasing the supersaturation of non-ionic Compound A. After this final pH adjustment, the suspension is advantageously stirred for some hours to enhance the precipitation of Compound A, e.g. 4–30 hours, preferably 8–20 hours. The precipitate should then be separated from the reaction mixture by a conventional technique, such as centrifugation or filtration, and optionally washed with a suitable solvent, e.g. water or methanol.

The filtrate from the separation mainly contains iodixanol and small fractions of related iodinated aromatic compounds, in addition to salts and remaining epichlorohydrin and derivatives thereof. This mixture can be purified by conventional desalination and crystallisation methods to obtain iodixanol suitable for pharmaceutical use. Chromatographic purification of the crude iodixanol in the filtrate is not necessary.

The separated Compound A from the recovery process can optionally be recrystallised, for example from water/methanol or another alkanol. Thus, the moist material from the filtration/centrifugation may be dissolved in water in the presence of alkali. The amount of water should be about 2–7 l/kg of Compound A, preferably 3–5 l/kg. Alkali, e.g. aqueous sodium hydroxide, should be added until all traces of undissolved material are removed. The solution may optionally be filtered to remove remaining traces of undissolved matter. An alcohol, e.g. methanol (0.5–1.5 l/kg of Compound A, preferably 0.5–1.0 liters/kg) may then be added, and the mixture heated to 40–80° C., preferably 50–60° C. Adjustment of pH by an acid, e.g. hydrochloric acid, causes pure Compound A to precipitate. The mixture may optionally be seeded with a small amount of Compound A crystals. Maximum yield from the recrystallisation is obtained if the pH is finally adjusted to about 5–7, e.g. with hydrochloric acid, followed by cooling to 10–25° C. The slurry may optionally be stirred at this temperature to enhance the crystallisation, e.g. 2–18 hours. The precipitate is separated from the suspension by any conventional technique, for instance centrifugation or filtration, and optionally washed with water, methanol or another suitable alkanol. The recovered Compound A may advantageously be dried, e.g. under reduced pressure, before reuse in a new dimerisation. Recovered Compound A, together if necessary with further fresh Compound A, may be used in a new dimerisation reaction as described above, followed by subsequent recovery of unreacted Compound A. The invention thus also includes process in which iodixanol is prepared in a series of successive processes according to the invention in which, after the dimerisation, unreacted Compound A is precipitated from the reaction mixture and recovered, optionally crystallised, and then re-used in a subsequent process in the series. The dimerisation reactions in such a series will normally be substantially identical, and the unreacted Compound A will normally be recovered after each dimerisation step.

The following examples illustrate the invention.

EXAMPLE 1

Compound A (366 g) was dissolved in a solution of NaOH(23 g) in 2-methoxyethanol (360 ml) at 50° C. The temperature was decreased to 15° C. when all solids were dissolved, and conc. HCl (28 g) was added to the solution. Epichlorohydrin (13 g) was added in one portion, and the reaction was monitored by HPLC. After 46 hours the content of iodixanol in the reaction mixture was 49.6%. Water (575 ml) was added, and the temperature was increased to 19° C. The solution was at this time clear, so no further addition of sodium hydroxide was necessary. The pH was adjusted to 10.8 by 18% hydrochloric acid, and the solution seeded with 1 g of Compound A. The pH of the resulting suspension was further pH-adjusted with 18% hydrochloric acid to pH 4.0. The suspension was left with stirring overnight before filtration and washing with water (60 ml) on the filter. The filtrate was further desalinated and crystallised by conventional methods, providing iodixanol suitable for pharmaceutical use. The material on the filter was analysed on HPLC, showing 94.3% Compound A and 5.1% iodixanol.

EXAMPLE 2

The recovered Compound A from Example 1 was taken directly from the filter without drying, and completely dissolved in water (440 ml) and 50% aqueous NaOH (15 ml). The solution was filtered through a 3 μm filter to remove traces of insoluble matter, and some more water (50 ml) was added to the filtrate. Methanol (95 ml) was added to the solution, and the temperature was increased to 60° C. The pH was reduced from 11.5 to 9.8 with 18% hydrochloric acid, and 0.8 g seeds of Compound A was added. After 30 minutes, the pH was further reduced to 6 with 18% hydrochloric acid. The temperature was gradually reduced to 15° C., and the precipitated material was filtered, washed with methanol (140 ml) and dried under vacuum at 60° C. The yield of pure Compound A (>99% by HPLC) was 118 g, corresponding to 32% of the starting material in Example 1.

The recovered Compound A (118 g) was combined with fresh Compound A (248 g) in a new dimerisation similar to Example 1, giving nearly identical results as in Example 1.

What is claimed is:

1. In a process for the preparation of iodixanol by dimerization of 5-acetamido-N,N'-bis(2,3-dihydroxypropyl)-2,4,6-triiodo-isophthalamide ("Compound A") the improvement comprising precipitating unreacted Compound A, after the dimerization, from the reaction mixture and recovering the precipitated unreacted Compound A for re-use.

2. The process of claim 1 wherein the dimerization step is carried out using epichlorohydrin; 1,3-dichloro-2-hydroxypropane; or 1,3-dibromo-2-hydroxypropane as the dimerisation agent in a solvent selected from the group consisting of non-aqueous solvents, water, and mixtures of water and one or more alcohols.

3. The process of claim 2 wherein the dimerization agent is epichlorohydrin and the solvent is 2-methoxyethanol or methanol.

4. The process of claim 1 wherein precipitation of Compound A is effected with water, optionally together with an alcoholic co-solvent.

5. The process of claim 4 in which the pH of the mixture is adjusted to 10–11 with acid to provoke precipitation and the temperature is adjusted, if necessary, to 15–40° C.

6. The process of claim 5 in which further acid is added to adjust the pH of the mixture to 2–5.

7. The process of claim 1 wherein the Compound A recovered is recrystallised.

8. The process of claim 1 in which, after the precipitation of unreacted Compound A, the iodixanol is purified without the use of chromatographic methods.

9. The process of claim 1 wherein the recovered Compound A is re-used in a subsequent process for the preparation of iodixanol.

* * * * *

UNITED STATES PATENT AND TRADEMARK OFFICE
CERTIFICATE OF CORRECTION

PATENT NO. : 6,974,882 B2 Page 1 of 1
DATED : December 13, 2005
INVENTOR(S) : Ole Magne Homestad It is certified that error appears in the above-identified patent and that said Letters Patent is hereby corrected as shown below:

<u>Column 2,</u>
Line 8, "(NO 161358)" should read -- (NO 161368) --.

Signed and Sealed this

Twenty-eighth Day of March, 2006

JON W. DUDAS
*Director of the United States Patent and Trademark Office*